US006942624B2

(12) United States Patent
Takizawa et al.

(10) Patent No.: US 6,942,624 B2
(45) Date of Patent: Sep. 13, 2005

(54) BIOLOGICAL INFORMATION DETECTION SYSTEM

(75) Inventors: Shun Takizawa, Nagano (JP); Yuichi Minamiyama, Nagano (JP); Hiroto Nakatani, Aichi (JP); Kenichi Yanai, Aichi (JP)

(73) Assignees: GAC Corporation, Toyoshina (JP); Denso Corporation, Kariya (JP)

( * ) Notice: Subject to any disclaimer, the term of this patent is extended or adjusted under 35 U.S.C. 154(b) by 0 days.

(21) Appl. No.: 10/602,815

(22) Filed: Jun. 25, 2003

(65) Prior Publication Data

US 2004/0000542 A1 Jan. 1, 2004

(30) Foreign Application Priority Data

Jun. 28, 2002 (JP) ....................................... 2002-189103
Jun. 28, 2002 (JP) ....................................... 2002-189104

(51) Int. Cl.[7] .................................................. A61B 5/08
(52) U.S. Cl. ........................ 600/534; 600/587; 600/529
(58) Field of Search ................................ 600/484, 485, 600/486, 487, 488, 534, 587; 174/50.5, 52.3; 439/892, 893, 894; 73/763, 764, 765, 766, 767, 768, 769, 770, 771, 772, 773, 774

(56) References Cited

U.S. PATENT DOCUMENTS 3,832,603 A * 8/1974 Cray et al. .................. 361/790
4,133,592 A * 1/1979 Cobaugh et al. .............. 439/74
5,448,996 A * 9/1995 Bellin et al. ................ 600/574
5,550,324 A * 8/1996 Black et al. ............... 174/52.3
5,785,659 A * 7/1998 Caro et al. .................. 600/485
6,095,844 A * 8/2000 Kasai ......................... 439/352
6,126,611 A * 10/2000 Bourgeois et al. .......... 600/529
6,210,339 B1 * 4/2001 Kiepen et al. .............. 600/486
6,592,528 B2 * 7/2003 Amano ....................... 600/485

* cited by examiner

*Primary Examiner*—Robin O. Evans
*Assistant Examiner*—L Fastovsky
(74) *Attorney, Agent, or Firm*—Posz Law Group, PLC

(57) ABSTRACT

The input/output system of the present invention includes a sheet-like input/output unit that includes wiring and a connection box that is attached to an edge of the sheet-like input/output unit. The connection box includes a housing that is attached so as to sandwich the sheet-like input/output unit and internally encloses a circuit board that is connected to the wiring. The housing includes a slit through which the sheet-like input/output unit passes and whose upper and lower edges are curved and means for fixing the sheet-like input/output unit that is disposed inside to the slit. Since the means for fixing the sheet-like input/output unit is disposed inside to the slit, the edges of the slit are narrow but formed with large radii of curvature, so that the sheet-like input/output unit is not folded over at the slit part. The slit can also be sealed by attaching packing to the edge of the slit.

10 Claims, 11 Drawing Sheets

BIOLOGICAL INFORMATION DETECTION SYSTEM

BACKGROUND OF THE INVENTION

1. Technical Field

The present invention relates to an input/output (input-output) system that includes a sheet-like input/output unit into which wiring is embedded or onto which wiring is stuck, and a connection box that is attached to the input/output unit.

2. Description of the Related Art

Electric carpets, electric blankets and electric underblankets are products that use a sheet-like member as an output unit and in the sheet-like output unit, wiring is embedded. In such products, a control box is attached to an edge of the sheet-like output unit as a connection box for controlling the power supplied to an embedded heater via the wiring. The connection box has a control function and/or a connection function. A housing of the connection box is divided into an upper housing and a lower housing so as to form a slit into which the output unit is fitted. The connection box is fixed onto the sheet-like output unit by hooks or projections that are provided on the upper and/or lower edges of the slit through which the output unit passes and grasp the output unit.

Electric carpets, electric blankets, and electric underblankets are all relatively thick and are extremely soft. This means that even if the sheet-like output unit is grasped by the hooks or projections, there is little risk of damage to the wiring embedded inside the wiring unit. There is also no risk of damage to the sheet-like output unit itself.

In recent years, sensor sheets, in which a plurality of sensors, such as pressure sensors, are embedded have been introduced. A sheet-like base material of the sensor sheet is a plastic sheet that is thin and soft, and relatively firm so as to be able to maintain its shape to a certain degree. By such a characteristic base material, thin semiconductor materials that operate as the pressure sensors are supported and disposed at predetermined intervals so that specified surfaces of the pressure sensors are oriented in a specified direction. The sensor sheet on which a plurality of pressure sensors are disposed can be used as a biological information detection apparatus that detects and/or monitors the breathing of a user on a bed. When spread on a bed and lain upon by a user, the biological information detection system including the sensor sheets can determine the biological or living state of the user by analyzing the output of the pressure sensors on the sensor sheets. This means by using a biological information detection system in a hospital it is possible to detect whether a gravely ill patient is breathing during emergencies and to measure the number of times a patient suspected of sleep apnea syndrome stops breathing during his or her sleep.

The biological or biomedical information detection system is one of input apparatus that uses a sensor sheet as an input unit, a connection box with a control and/or a connection function for receiving an input of signals from the sensors via the wiring of the input unit is required. In an input apparatus for receiving important information such as the biological information detection apparatus, damage and breakages of the wiring have a large effect on the reliability of apparatus or system. On the other hand, when bed making or the system is not in use, it is important to be able to fold up the sheet-like input unit (sensor sheet) since the sheet occupies large area. When the sensor sheet is folded up, the boundary part of the connection box and the sensor sheet becomes folded part and the wiring of the boundary part are damaged. In addition, a firm, thin plastic base sheet may be snapped by bending a sharp angle. Even if the sheet is not folded or snapped at beginning, the sheet can become creased, and if the sheet is repeatedly bent at such positions, stresses become concentrated, which makes it easy for the wiring to become damaged.

In order to pull a sheet-like input/output unit such as the sensor sheet into the connection box, a slit-like opening has to be provided. If the shapes of the edge parts of this slit-like opening is curved and the curvature is small and radius is large, the sheet-like input/output unit can be prevented from being bent sharply, so that the concentration of stresses can be avoided. However, to increase the radius of curvature, it is necessary to increase the area of the edge parts of the slit. In addition, if hooks or projections for fitting and fixing the sheet-like input/output unit are provided on the edges of the slit, it is necessary to provide sufficient plain area for forming the hooks or projections within the edge area. This means that the area of the edge parts of the slit becomes extremely large and complex, so that it is not possible to make the connection box compact.

Instead of providing a means, such as hooks or projections, for fixing the sheet-like input/output unit on the edge of the slit, it is possible to fix the input/output unit and connection box by merely connecting the wiring of the input/output unit to a terminal box inside the connection box, which makes it possible to make the connection box compact. However, when some force acts so as to separate the sheet-like input/output unit and the connection box, such force is concentrated on the joined parts of the wiring and the terminal block inside the connection box, and leads to poor electrical contact.

As mentioned, there are strong demands for the ability to store input/output systems, which include a sheet-like input/output unit, in a compact manner when the systems are not in use. If an input/output system is stored without bending the part where the connection box is attached, it is not possible to make the storage state of the input/output system compact. It is not possible to store the input/output system in an especially compact form by merely folding the sheet-like member. Also, when a relatively firm plastic sheet is used as the base material so as to make it possible for the sheet-like input/output unit to retain its shape to a certain degree, it is not very easy to fold up the sheet-like input/output unit without folding the boundary of connection box.

For the above reasons, it is an object of the present invention to provide an input/output system in which a sheet-like input/output unit is reliably attached to a connection box without the wiring embedded or stuck onto the sheet-like input/output unit becoming damaged when some forces may act thereto. It is a further object of the present invention to provide an input/output system that can be easily and safely (without damage) placed into a compact form during storage.

SUMMARY OF THE INVENTION

An input/output system (or "bioloaical information detection system") according to the present invention includes a sheet-like input/output unit (or "sensor unit") that includes wiring and a connection box that is attached to an edge of the sheet-like input/output unit, wherein the connection box includes a housing that is attached so as to sandwich the sheet-like input/output unit and internally encloses a circuit board that is connected to the wiring. The housing includes:

a slit through which the sheet-like input/output unit passes and whose upper and lower edges are rounded or curved shape; and a means for fixing the sheet-like input/output unit that is disposed inside to the slit. The sheet-like input/output (input-output) unit may be a unit that performs only input or only output, or a unit that performs input and output. The input/output (input-output) system may be a system that performs only input or only output, or a system that performs input and output.

In the connection box of the input/output system, a fixing means such as hooks or projections for fixing the sheet-like input/output unit is disposed on the inside to the slit of the housing. This is to say, in the connection box of the present invention the means for fixing, such as hooks or projections, is disposed inside the housing, not at the edge of the slit. This means that there are no surface irregularities such as hooks or projections at the edges of the slit. Therefore, the shape of edges are simple and the radius of curvature can be increased even if the edges are narrow, that means the width of the edges of the slit will not become wide or wider so much for increasing the radius of edges. Accordingly, even if attempts are made to fold over the part of the sheet-like input/output unit at the edge of the slit, the concentration of the bending stresses can be prevented and it becomes possible to prevent the sheet-like input/output unit itself and the wiring from damage. The sheet-like input/output unit is reliably fixed inside the housing by the means for fixing, so that even if a force is applied between the sheet-like input/output unit and the connection box, the force does not act on the connected parts of the wiring and the wiring does not suffer from breakages.

Accordingly, even if the sheet-like input/output unit is a firm but thin sensor sheet that is made of plastic or the like, the sheet-like input/output unit can be compactly stored by bending the sheet-like input/output unit without causing folds at the part where the connection box is attached. The sheet-like input/output unit becomes durable even when bent repeatedly at the connection box. Even if the part of the sheet-like input/output unit that is attached to the connection box is bent, the edges of the slit are curved or rounded in the directions in which the sheet-like input/output unit passes, so that even if the sheet-like input/output unit is bent or attempted to fold, this does not result in a sharp angle and the wiring that is embedded in or stuck onto the sheet-like input/output unit is not damaged. This means that it is possible to provide an input/output system that has a sheet-like input/output unit and is easy to handle and highly reliable.

With the connection box of the present invention, a sheet-like input/output unit can be reliably fixed to the connection box without providing concave and convex parts at the edges of the slit. Accordingly, it is possible to form an elastic sealing part, which is made of rubber or the like, on at least one of the upper and lower edges of the slit of the housing. By making at least one of the edges elastic, the elastic edge(s) of the slit can sandwich the input/output unit and seal the inside of the housing. When a sensor sheet is used as a biological information detection system, there are cases where the subject who lies on the sensor sheet is incontinent. In such applications, there is the risk of moisture seeping into the connection box from the surface of the sheet-like input/output unit. Accordingly it is extremely effective to make the connection box water resistant by sealing the slit for pulling the sheet-like input/output unit into the connection box.

The most suitable means for fixing the sheet-like input/output unit is one or more projections. By providing holes in advance for inserting the projection(s) in a part or an area of the sheet-like input/output unit that is sandwiched by the housing, it is possible to easily fix the sheet-like input/output unit without damaging the sheet-like input/output unit.

It is also preferable for the circuit board to which the wiring is connected to be provided with means for fixing a covering material of the wiring to the circuit board. By fixing the sheet-like input/output unit to the connection box and also fixing the covering material of the wiring to the circuit board, the connection between the wiring and the circuit board can be provided with double protection. Accordingly, even if the sheet-like input/output unit disengages t from the housing, a force is not immediately applied to the connection between the wiring and the terminals, so that it is possible to provide a highly safe connection box where the wiring is reliably connected. The input/output system is suited to applications where high reliability is required, such as a biological and/or biomedical information detection system.

Also, in a connection box in which a plurality of circuit boards are stacked one on top of another inside the housing, it is preferable for the circuit board to which the wiring of the sheet-like input/output unit is connected to be the lowest circuit board. Since there are few circuit boards provided below the sheet-like input/output unit, the thickness of the connection box that projects below the sheet-like input/output unit can be reduced. Accordingly, when the sheet-like input/output unit is spread out on a bed or the like, the height of the slit of the connection box is almost equal to the height of the slit, so that the sheet-like input/output unit can be prevented from being lifted up near the connection box. Also, by reducing the bending of the sheet-like input/output unit, unexpected force that is caused by such bending does not act at the connecting part of the sheet-like input/output unit and the connection box, thereby increasing the reliability of the wiring. Additionally, with the above biological information detection system, it is possible for the subject to lie on the sheet-like input/output unit even near the connection box without experiencing any discomfort, so that the sheet-like input/output unit can be put to effective use for a wide range of detections and measurements.

In cases where the input/output system is used as a biological information detection system, one of the most suitable forms for the sheet-like input/output unit is to have a data input region in which piezoelectric sensors are disposed and a wiring region that is disposed along one edge or side of the data input region. In addition, there are demands for input/output systems of that cover a wide range of sizes of bedding, which for the example of beds can be "single", "semi-double" and "double". Accordingly in an input/output unit including a data input/output region that is equipped with a function for inputting and/or outputting data and a wiring region that is disposed along at least one side of the data input/output region, it is preferable to dispose first wiring, which extends from the data input/output region to a first edge of the sheet-like input/output unit, and second wiring, which is not connected to the data input/output region and extends from the first edge of the sheet-like input/output unit to a second edge opposite the first edge, in the wiring region.

With this sheet-like input/output unit, the second wiring that is not connected to the data input/output region is used to connect a second input/output unit without providing new wiring materials, so that the area that can be covered by the sheet-like part can be increased easily. The second input/output unit can be connected through the first sheet-like input/output unit, by the second wiring, to the connection box attached to the first edge of the first sheet-like input/output unit. Accordingly, the area of the input/output unit can be increased easily in units of sheet-like input/output units with a small area. Also, it is possible to use a connection box that is shared by the first and second input/output units. This means that it is possible to provide an input/output system that has wide applicability, high productivity with favorable yields, high reliability at low cost, and an area that can be changed flexibly. Since the sheet-like input/output unit can be dismantled into small units, storage becomes simpler.

The second wiring may overlap the first wiring. By disposing the second wiring on the opposite side of the first wiring to the data input/output region, the first and second wiring can be arranged on a single plane without crossing one another. Accordingly, the wiring region can also be made extremely thin, so that there is no risk of the wiring becoming displaced when the first and second wiring are integrated with the sheet-like input/output unit. In applications where the sheet-like input/output unit is spread on a bed, such as with a biological information detection system, discomfort caused by the wiring can be suppressed.

An arrangement is preferable that on the first edge, the first wiring and the second wiring are parallel, and on the second edge, the second wiring is disposed at a position corresponding to the position of the first wiring on the first edge. By disposing a first sheet-like input/output unit and a second sheet-like input/output unit so that the first edge and the second edge face one another, the first wiring of the second sheet-like input/output unit will face the second wiring of the first sheet-like input/output unit. Accordingly, the wiring can be connected in an extremely easy operation.

It is also possible to dispose third wiring, which is not connected to the data input/output region and extends from the first edge to the second edge of a sheet-like input/output unit, in the wiring region of the sheet-like input/output unit, and in the same way, fourth or subsequent wiring can also be disposed. In this way, by increasing the wiring that is not connected to the data input/output region, it is possible to easily connect a third, fourth, or subsequent sheet-like input/output unit in the same way as above. Accordingly, the area that is covered by a sheet assembly in which a plurality of sheet-like input/output units are connected can be flexibly changed. The plurality of sheet-like input/output units can all be controlled and data can be inputted and outputted by a single connection box.

One example of the sheet-like input/output unit is a sensor sheet in which a plurality of piezoelectric sensors are disposed in the data input/output region of the sheet-like input/output unit. An input/output system of a suitable size for a bed and/or for the body of a subject such as an adult or an infant can be constructed easily from a number of sensor sheets, with this input/output system being provided at low cost. The present invention is not limited to pressure sensor sheets, and can be applied to an input system that has another kind of sensors disposed in the data input/output region and to a sheet-type output system where a plurality of data output elements, such as EL elements, are disposed in a data input/output region.

It is also preferable for curved cut parts to be provided corresponding position or positions of opposite edges of the sheet-like input/output unit. The input/output system can be bent further at these curved cuts, so that the input/output unit can be placed into a compact state for storage or carrying.

BRIEF DESCRIPTION OF THE DRAWINGS

These and other objects, advantages and features of the invention will become apparent from the following description thereof taken in conjunction with the accompanying drawings which illustrate a specific embodiment of the invention. In the drawings:

FIG. 6A is a partial enlarged cross-sectional view showing one example of a control box to which cylindrical packing has been attached, while

DESCRIPTION OF THE PREFERRED EMBODIMENT

Figure 1:
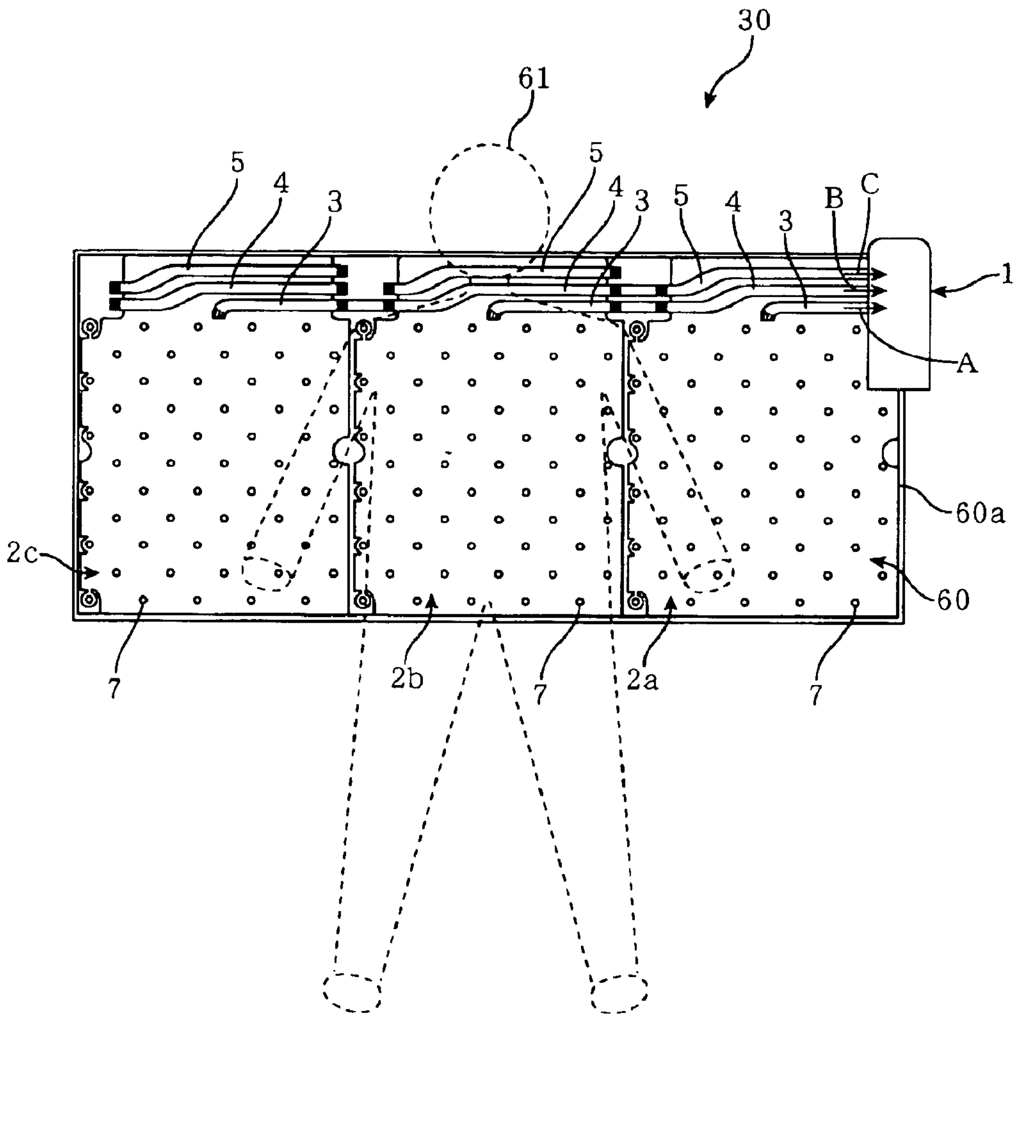
FIG. 1 shows an example of a biological information detection system that uses a control box according to the present invention.

FIG. 1 shows sensor sheets 2*a* to 2*c*, in which a plurality of pressure sensors (piezoelectric sensors) 7 that use piezoelectric elements are disposed in an array, and a biological information detection system 30 that uses these sensor sheets 2*a* to 2*c*. In the present embodiment, the three sensor sheets 2*a*, 2*b*, and 2*c* are the sheet-like input units of the present invention, and the biological information detection system 30 is an input system of the present invention that obtains data from a plurality of pressure sensors. Accordingly, the following describes the present invention by way of an input system that includes an input unit as one example of an input/output system. The three sensor sheets 2*a*, 2*b*, and 2*c* each have the same construction and are connected in the horizontal direction in the drawing to form a large sheet assembly 60. On one edge 60*a* of this sheet assembly 60, a control box 1 with a control function is attached and connected to pressure sensors 7 via wiring 3, 4, and 5. This control box 1 corresponds to the connection box of the present invention.

The sensor sheets 2*a*, 2*b*, and 2*c* are referred to below as the sensor sheet 2 when their common construction is being described. The sensor sheet 2 has a thin plastic sheet as its base material, and a plurality of piezoelectric elements 7 that form the pressure sensors are disposed regularly at appropriate intervals. Wiring for obtaining outputs from these pressure sensors 7 is also disposed or formed in the sensor sheet 2. The pressure sensors 7 of the sheets 2 are provided at predetermined positions or predetermined intervals, and are disposed with a predetermined orientation that is suited to measuring pressure. Therefore, by this biological information detection system, the biological (biomedical or living) state of a user (subject) via the sensor sheet 2 even if the pressure sensors are not directly attached to the user who lies on the sensor sheet 2. The sheet assembly 60 is spread out on a bed, the breathing state or other state of the user 61 on a bed who lies on the sheet assembly 60 is sensed and the control box 1 stores the signals collected from the individual pressure sensors 7 of the sensor sheets and monitors the state of the user (patient) by analyzing these signals.

The sheet assembly 60 includes three sensor sheets 2*a*, 2*b*, and 2*c* and the signals C from the individual pressure sensors 7 of the sensor sheet 2*c* that is located furthest from the control box 1 are transmitted to the control box 1 via the wiring 4 of the sensor sheet 2*b* and the wiring 5 of the sensor sheet 2*a* that are positioned in between. The signals B from the individual pressure sensors 7 of the sensor sheet 2*b* are transmitted to the control box 1 via the wiring 4 of the sensor sheet 2*a* that is positioned in between. The signals A from the individual pressure sensors 7 of the sensor sheet 2*a* to which the control box 1 is attached are collected by the control box 1 via the wiring 3 of the sensor sheet 2*a*.

Figure 2:
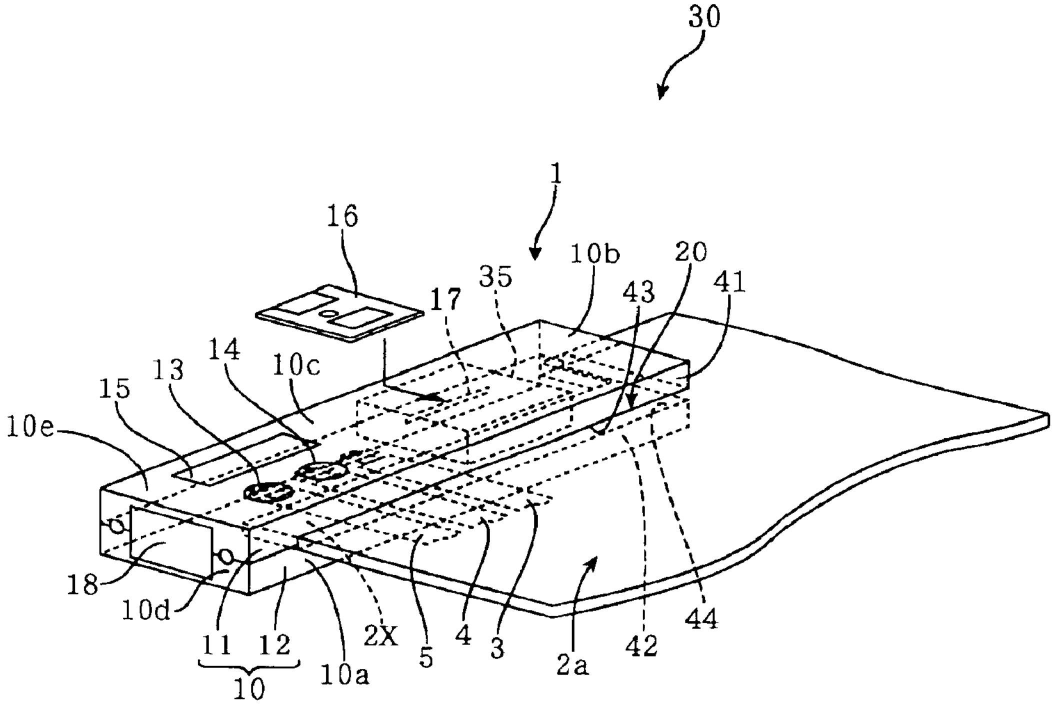
FIG. 2 is a perspective view showing how a sheet-like input/output unit is attached to the control box.

FIG. 2 is a perspective view showing how the sensor sheet 2*a* is attached to the control box 1. The control box 1 includes an almost flat housing 10 that is approximately rectangular. A circuit board 31, a battery 35, and other electrical components that are required for display and operations are enclosed in this housing. To the circuit board 31, the wiring 3, 4, and 5 that is disposed in parallel on the sensor sheet 2*a* is connected in a parallel state. When upper and lower housings 11 and 12 are assembled on top of one another, a slit 20 is continuously formed around two adjacent side surfaces 10*a* and 10*b* out of four side surfaces 10*a*, 10*b*, 10*c* and 10*d*, with the slit allowing the sensor sheet 2 to pass through to the inside of the housing 10. Accordingly, by sandwiching the sensor sheet 2*a*, which is a sheet-like input unit, between the upper housing 11 and the lower housing 12, the housing 10 can be attached to an edge (a corner part of the edge in the illustrated example) 2*x* of the sensor sheet 2*a*. By attaching the control box 1 to the corner part or area 2*x* of the edge of the sensor sheet 2*a*, the wiring 3, 4, and 5 of the sensor sheet 2*a* is introduced into housing 10.

A switch 13 and a switch 14 for recording the signals A, B, and C from the pressure sensors and a LCD (liquid crystal display) 15 that is capable of displaying the recording state, etc., are disposed on an upper surface 10*e* of the housing 10. A slot 17 for inserting a recording medium 16 is provided on an opposite side surface 10*c* to the slit 20, while a communication connector 18, which can be connected to an external information processing apparatus such as a personal computer, is provided on the side surface 10*d*. Accordingly, the signals A, B, and C from the pressure sensors can be supplied to and recorded by the recording medium 16 and/or the external information processing apparatus.

Figure 3:
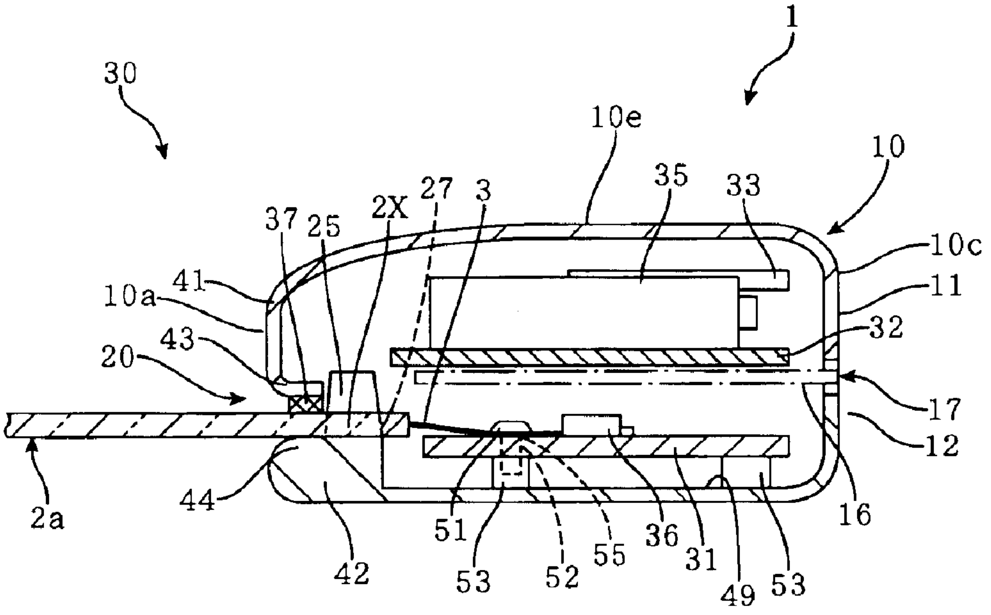
FIG. 3 is a cross-sectional view showing the internal construction of the control box.
Figure 4:
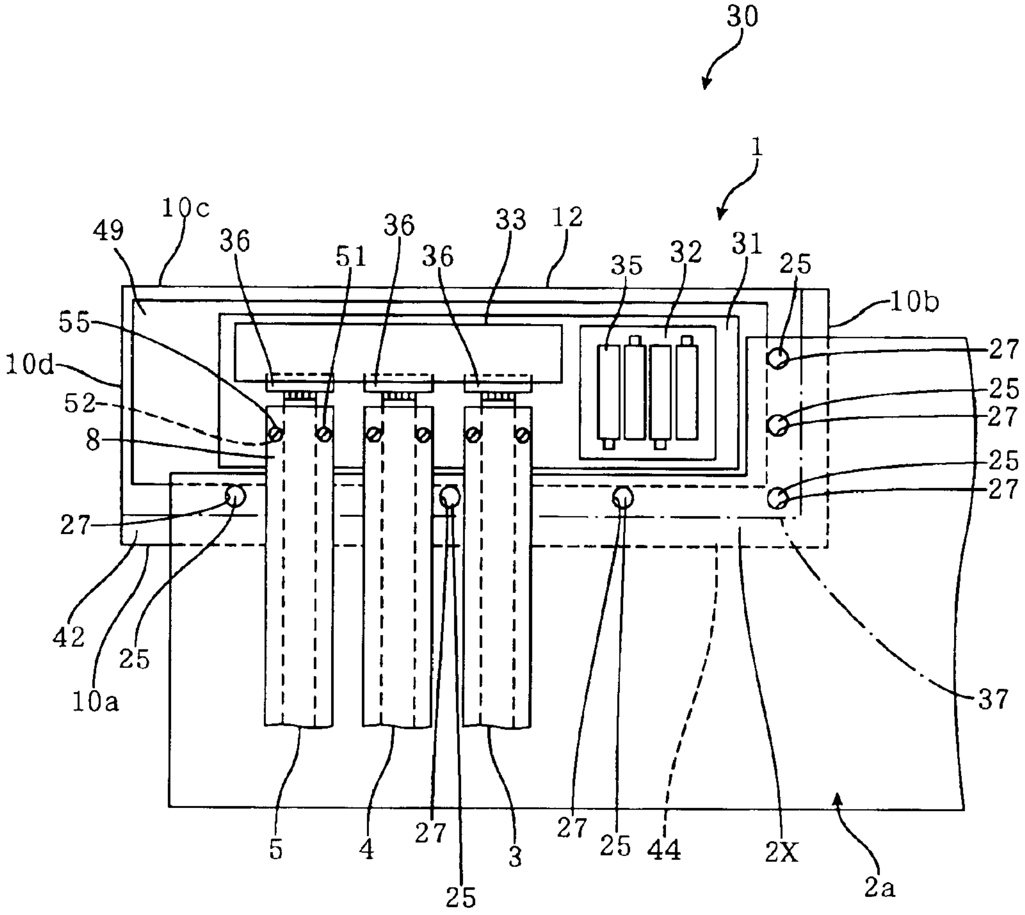
FIG. 4 shows the control box in a state where the upper housing has been removed.

FIG. 3 is a simplified cross-sectional view showing the inside of the housing 10 of the control box 1. FIG. 4 shows the inside from above when the upper housing 11 of the housing 10 has been removed. A circuit board 31 to which the wiring 3, 4, and 5 is connected, a circuit board 32 to which a battery 35 is connected, and a circuit board 33 for controlling the liquid crystal display 15 are provided one on top of another starting from the bottom in the stated order inside the housing 10. Three connectors 36, to which the wiring 3, 4, and 5 is connected, are mounted on the lowest circuit board 31, which is supported by a plurality of bosses 53 on a base surface 49 of the lower housing 12. Accordingly, the wiring 3, 4, and 5 can be connected to the circuit board 31 at a height that is close to the base surface 49 of the lower housing 12, with the slit 20 through which the sensor sheet 2 passes being formed in accordance with this height.

An upper edge of the slit 20 is composed of a lower end 43 of a side wall 41 the upper housing 11, with this lower end 43 being formed so that the side wall 41 is curved with a large radius of curvature on an inside of the housing 10. A lower edge of the slit 20 is composed of an upper end 44 of a side wall 42 of the lower housing 12, with this upper end 44 being machined into an almost cylindrical shape with a large radius of curvature. Accordingly, the upper and lower edges 43 and 44 that compose the slit 20 both have a large radius of curvature, so that even if the sensor sheet 2 that is a firm, thin plastic sheet bends around these edges 43 and 44, the sensor sheet 2 bends in keeping with or about the edges 43 and 44, thereby preventing the sensor sheet 2 from folding over or snapping. According to experiments conducted by the inventors of the present invention, the sheet-like input unit 2 can be prevented from folding over by setting the radii of curvature of the edges 43 and 44 at 5 mm or above (R5 or above). Accordingly, by using the control box 1, when the part of the sensor sheet 2 to which the control box 1 is attached is bent or attempted to fold onto another part of the sheet-like input unit 2, the attached part always deforms without the sheet-like input unit 2 itself being folded over, so that the wiring 3, 4, and 5 is not subjected to damage and breakages do not occur.

Out of the edges 43 and 44 above and below the slit 20, a rubber packing 37 is attached to the upper edge 43 as a sealing member. The upper edge 43 of the slit 20 is in fact composed of the packing 37 that is curved along the lower end of the side wall 41, and is an elastic sealing part. Accordingly, due to the packing 37 that extends downwards from the lower end 43 that is above the slit 20, the sensor sheet 2 tightly contacts the upper end 44 of the side wall 42 that is below the slit 20. When the sensor sheet 2 is held in the slit 20, the packing 37 that forms the upper edge 43 of the slit 20 tightly contacts a front surface of the sensor sheet 2 and a rear surface of the sensor sheet 2 tightly contacts the lower edge of the slit 20, so that the slit 20 is sealed. The slit 20 of the control box 1 can pass the sensor sheet 2 and also can be sealed in a state where the sensor sheet 2 has been inserted. Accordingly, the housing 10 is highly water resistant, so that even if water is spilled on the sensor sheet 2, the water is prevented from seeping into the housing 10.

A plurality of projections (bosses) 25 that project upwards inside the lower end 43 of the side wall 41 of the upper housing 11 that forms the upper edge of the slit 20 are formed inside the upper end 44 of the side wall 42 of the lower housing 12 that forms the lower edge of the slit 20. Holes 27 are provided in advance in the sensor sheet 2 at positions that are inserted into the housing 10 and correspond to the bosses 25. A corner 2× of the sensor sheet 2 is inserted into the housing 10 via the slit 20, the holes 27 of the sensor sheet 2 engages the bosses 25, and the bosses 25 can fix the sensor sheet 2 onto the lower housing 12. In addition, when the upper housing 11 is attached, the sensor sheet 2 is sandwiched between the packing 37 that is stuck onto the lower end 43 of the side wall 41 of the upper housing 11 and the upper end 44 of the side wall 42 of the lower housing 12, so that it becomes difficult to pull out the sensor sheet 2.

A boss 27 is disposed inside to the packing 37 and the upper edge 44 of the side wall 42 that faces to the packing 37 on below the slit 20 in the control box 1. Accordingly, the packing 37 or lower end 43 of the upper side wall 41 and the upper end 44 of the lower side wall 42, those form the upper and lower edges of the slit 20, are formed as smoothly bent or curved surfaces with no convexes and concaves, which makes it easy to seal the slit 20. In addition, the packing 37 or the lower end 43 of the upper side wall 41 and the upper end 44 of the lower side wall 42 can be formed so as to be uniform in cross-section, which facilitates a large setting of the radius R. This is to say, it is easy to form the lower end 43 of the upper side wall 41 and the upper end 44 of the lower side wall 42 with large radii of curvature even if they are narrow, so that the sensor sheet 2 that passes through the slit 20 can be bent without being subjected to so much concentration of stress at the entrance of the slit 20.

The biological information detection system 30 can also be used to monitor sick adults and infants. Accordingly, depending on the way in which the biological information detection system 30 is used, there is the possibility of drinks being spilt on the sensor sheet 2 and of the patient being incontinent. Therefore, superior water-resistance is important for the biological information detection system 30 to operate stably.

The biological information detection system 30 is used with the sensor sheet 2 spread out on a bed. When the biological information detection system 30 is not necessary or when the bed is being made, the system 30 is convenient since it can be easily taken off. When doing so, the part of the sensor sheet 2 at the boundary with the control box 1, which is to say the part in front of the slit 20, bends easily and so is not subjected to damage. Also when the biological information detection system 30 is put away for storage, the part of the sensor sheet 2 in front of the slit 20 can be bent and the system 30 can be placed in a compact state without damage. When the part of the sensor sheet 2 in front of the slit 20 of the control box 1 is bent, the sensor sheet 2 bends gradually in keeping with the shape of the edges of the slit 20, so that the sensor sheet 2 does not become creased or folded over and the wiring 3, 4, and 5 is not subjected to damage. This means that the biological information detection system 30 is very durable and is highly reliable.

The circuit board 31 to which the wiring 3, 4, and 5 is connected is disposed on the lowest level in the housing 10. Therefore, the sensor sheet 2 is connected via the slit 20 at a height that is close to the base surface 49 of the housing 10 and approximately horizontal to the circuit board 31. This prevents the sensor sheet 2 from being pushed upwards near the slit 20 of the control box 1 when the sensor sheet 2 and the control box 1 are placed on a bed. When a user lies down near the control box 1, parts of the sensor sheet 2 that are pushed upwards by the user's body do not cause much discomfort for the user. Accordingly, it is possible to perform detection right up to positions close to the control box 1 of the sensor sheet 2.

Since there is little difference in height between the surface of the bed and the slit 20, even if a force acts so as to push the sensor sheet 2 downwards near the slit of the slit 20, there is little deformation in the sensor sheet 2. Accordingly, even if the user lies down close to the control box 1, little load or force is placed on the wiring 3, 4, and 5 so that this does not cause breakages.

Figure 5:
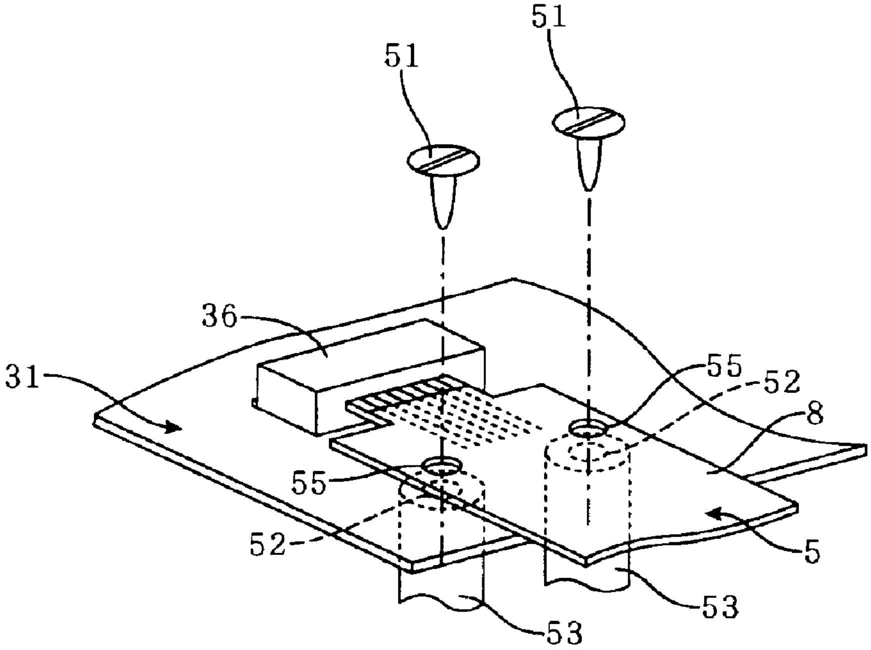
FIG. 5 shows how the circuit board and the wiring are fixed.

A plurality of holes 52 through which rivets and clips 51 pass are formed in the circuit board 31 to which the wiring 3, 4, and 5 is connected inside the control box 1. As shown in FIG. 5, by inserting fixings such as rivets, clips or screws 51 into holes 55 that are formed in covers 8 (covering materials or insulating coverings) of the wiring 3, 4, and 5 and the holes 52 of the circuit board 31, the circuit board 31 and the wiring 3, 4, and 5 can be fixed together respectively. In addition to the housing 10, by providing a means for fixing the wires on the circuit board 31, even if an extremely strong force is applied and the sensor sheet 2 comes away from the bosses 25, this in itself does not cause the wiring 3, 4, and 5 to come away from the circuit board 31. Accordingly, breakages can be reliably prevented for the wiring 3, 4, and 5, which make it possible to raise the reliability of the biological information detection system 30. This is a favorable construction for the biological information detection system 30 where faulty operation can lead to life-threatening problems.

Figure 6A:
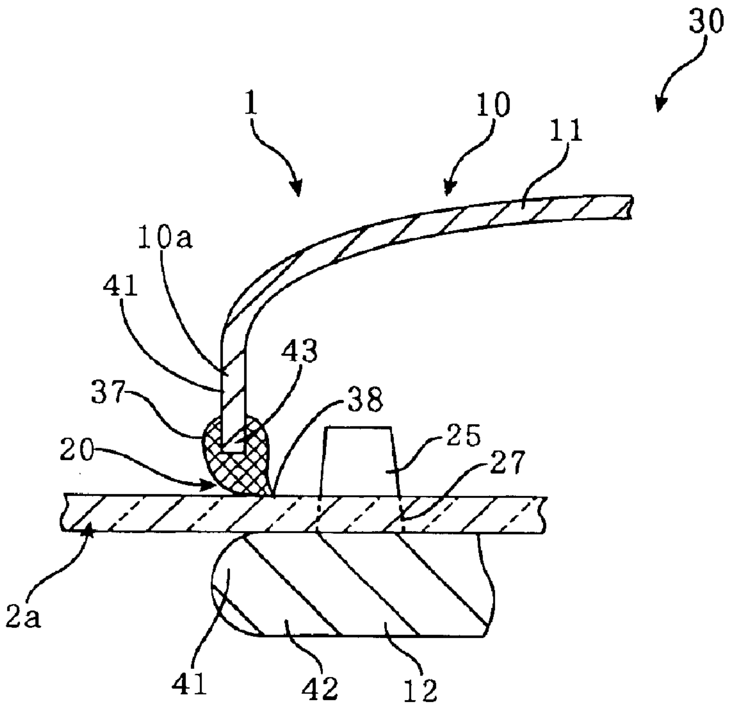

In the above description, the lower end 43 of the upper side wall 41 and the upper end 44 of the lower side wall 42 that form the edges of the slit 20 are rounded and packing 37 is attached to the lower end 43 of the upper side wall 41 so as to assume the shape of the lower edge 43. A material that is firm enough to maintain its own shape and can deform sufficiently on coming into contact with the upper end 44 may be used as the packing 37. In FIG. 6A, the radius of curvature of the form of the edge of the slit 20 is made large by the packing 37 in a rounded shape, such as a cylinder, with a large radius of curvature. Namely, In FIG. 6A, cylindrical packing 37 that covers the lower end 43 of the side wall 41 of the upper housing 11 is attached and forms a bent edge without the lower end 43 itself being rounded. In addition, by providing a fin-shaped projecting part 38 on the packing 37, the fin-shaped part 38 becomes an easier deformable part, which contacts the sensor sheet 2 or the lower edge 44 and improves the seal. The packing 37 and projecting part 38 are also elastic (flexible). When there are convexes and concaves in the surface of the sensor sheet 2 due to causes such as the wiring 3, 4, and 5 being stuck onto the surface of the sensor sheet 2, the packing 37 and projecting part 38 can deform in accordance with such concaves and convexes and sufficiently maintain the seal. The packing 37 and 38 deform in accordance with the shapes of the wiring 3, 4, and 5, so that the wiring itself is not subjected to damage.

Figure 6B:
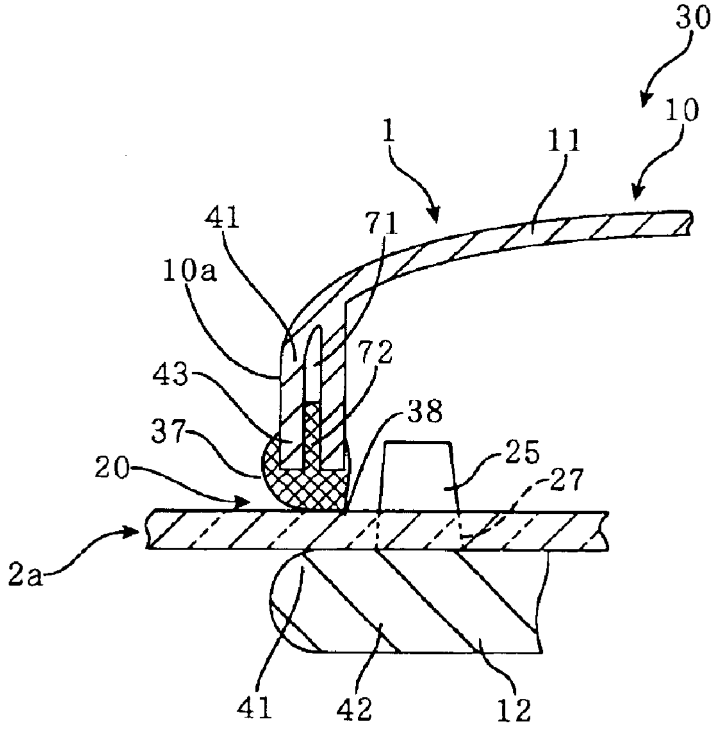
FIG. 6B shows a different example of a control box.

There are also various different ways to attach the packing 37. The packing 37 may be stuck on the lower end 43, as in the example shown in FIG. 3, or the packing 37 may be attached by fitting the lower end 43 into the packing 37, as in the example shown in FIG. 6A. In the example shown in FIG. 6B, a slit 71 is provided in the lower edge 43 and the packing 37 is attached by inserting a part 72 of the packing 37. Depending on the application, the attachment position of the packing 37 can also be set as the upper end 44 of the side wall 42 of the lower housing 12.

Figure 7:
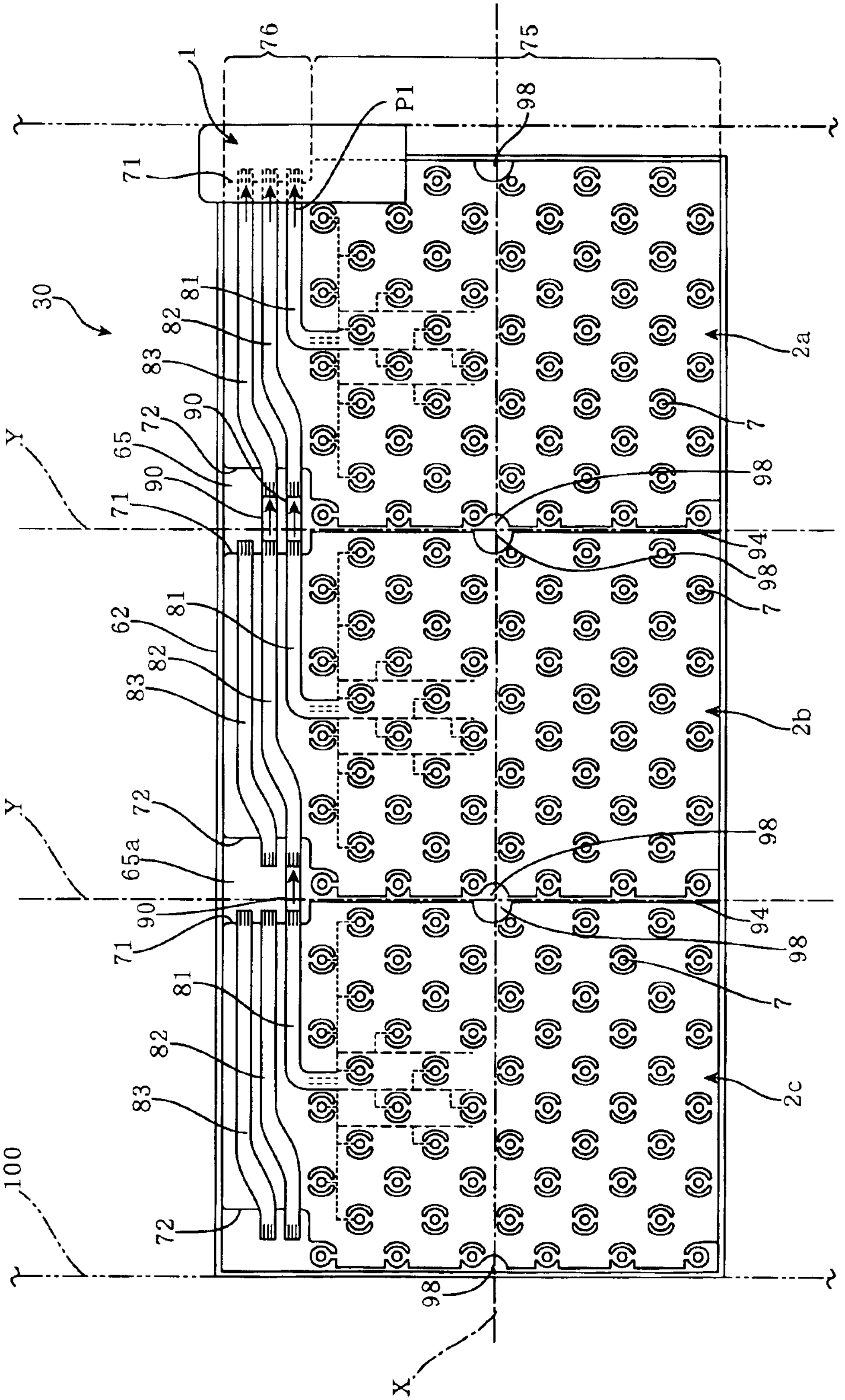
FIG. 7 is a plan view of the biological information detection system shown in FIG. 1.
Figure 8:
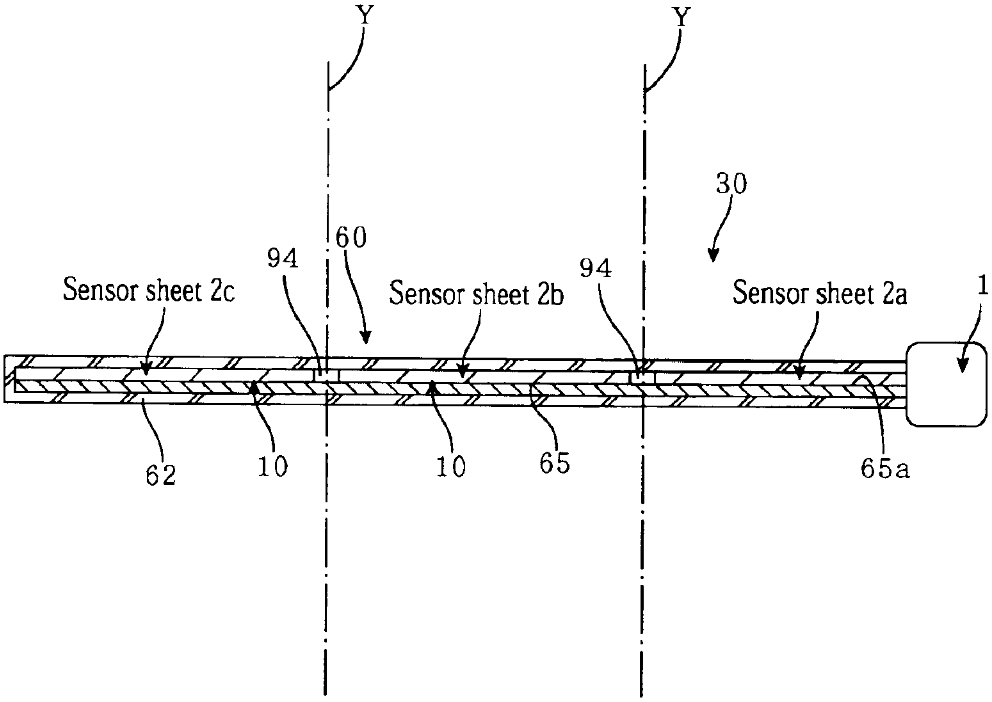
FIG. 8 is a cross-sectional view of the biological information detection system shown in FIG. 1.

FIG. 7 shows a state where the sheet assembly 60, in which the first sensor sheet 2*a*, the second sensor sheet 2*b*, and the third sensor sheet 2*c* are connected, has been spread out on a semi-double bed 100. A cross-sectional view of the sheet assembly 60 is shown in FIG. 8. The sheet assembly 60 is formed with a flexible base sheet 65 of the desired size as a core and has the three sensor sheets 2*a*, 2*b*, and 2*c* stuck onto a surface 65*a* of the base sheet 65 using double-sided tape or the like. In addition, once the sensor sheets 2*a*, 2*b*, and 2*c* have been stuck onto the base sheet 65, the base sheet 65 is covered by a bag-like sheet cover 62, thereby forming the sheet assembly 60. The control box 1 is attached to one end of the sheet assembly 60.

Figure 9:
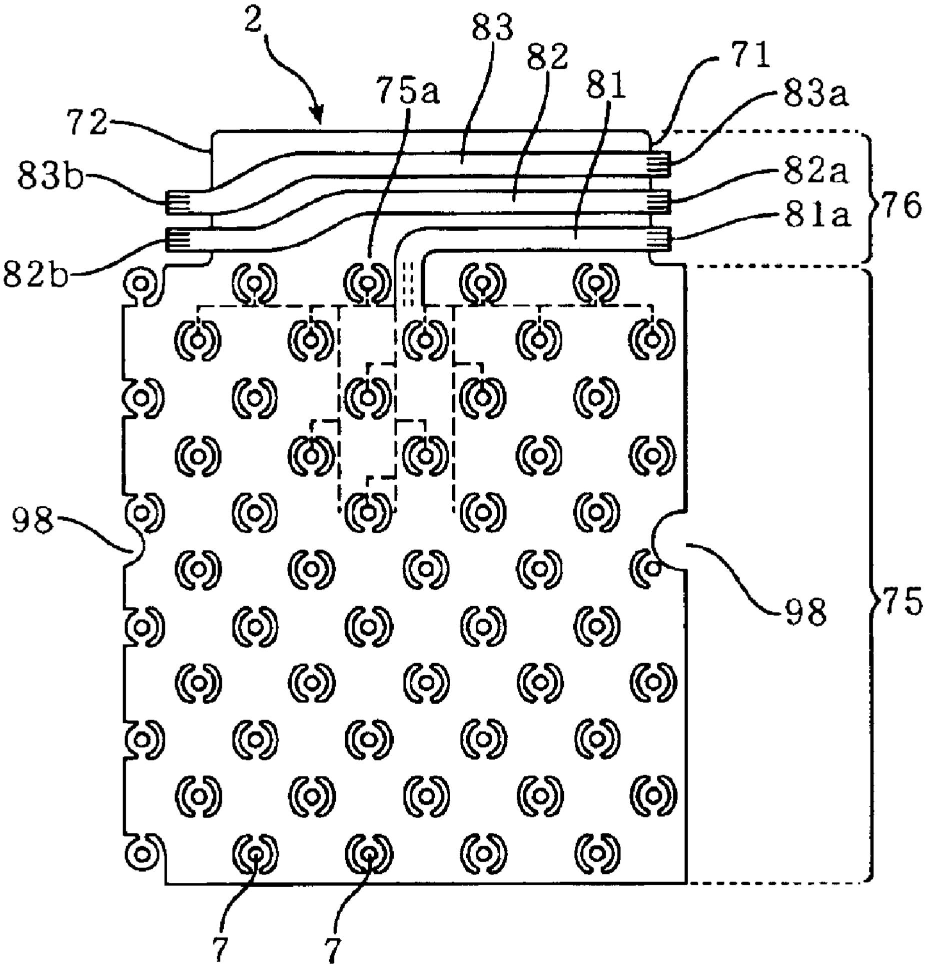
FIG. 9 shows an enlargement of the sensor sheet.

FIG. 9 shows the sensor sheet 2 simply. The sensor sheets 2 are approximately in the shape of rectangles along the longitudinal-direction of the bed 100. Therefore, the three sensor sheets 2*a*, 2*b*, and 2*c* are connected in a row in the lateral-direction (the horizontal direction) of the bed 100 to compose a sheet assembly 60 for cover the width of the bed 100. The sensor sheet 2 is provided with a data input region 75 in which a plurality of piezoelectric sensors 7 are laid out and embedded and a wiring region 76 that is disposed along an upper side 75a of the data input region 75. Three sets of printed wiring 81, 82, and 83 are disposed in the planar in the wiring region 76. This wiring 81, 82, and 83 can be formed by printing an electrode pattern on the sensor sheet 2 or by sticking on flexible cables.

The first wiring 81 extends from the center of the upper side 75a of the data input region 75 to an upper side of right edge (the first edge) 71 of the sensor sheet 2 in the drawing. The first wiring 81 is a wire set in which a plurality of wires extend in parallel, with the individual wires being respectively connected to the plurality of piezoelectric sensors 7 that are disposed of the data input region 75. Accordingly, the output of each of the piezoelectric sensors 7 can be externally outputted via the first wiring 81.

The second wiring 82 is wiring that extends from the right edge 71 of the sensor sheet 2 to the opposite left edge 72 (the second edge) of the sheet 2 and is not connected to the data input region 75. This second wiring 82 is wiring for extension purposes. This second wiring 82 is disposed on the opposite side of the first wiring 81 to the data input region 75, and the part that is adjacent to the first wiring 81 is disposed in parallel to the first wiring 81. The part of the second wiring 82 that is away from the first wiring 81, which is to say the part from the center of the upper side 75a of the data input region 75 to the left edge 72, is disposed with a gentle curve towards the data input region 75 so as to be arranged on a straight line with the first wiring 81. The left end 82b of the second wiring 82 is positioned opposite the right end 81a of the first wiring 81. Therefore, on the right edge 71, the first wiring 81 and the second wiring 82 are disposed parallel, and on the left edge 72, the second wiring 82 is disposed at a position corresponding to a position of the first wiring 81 on the right edge 71.

The third wiring 83 is wiring that extends from the right edge 71 of the sensor sheet 2 to the left edge 72 and is not connected to the data input region 75. This third wiring 83 is wiring for extension purposes. The third wiring 83 is disposed further outside the second wiring 82 and is disposed parallel to the second wiring 82. Accordingly a left end 83b of the third wiring 83 is positioned opposite the right end 82a of the second wiring 82. This means the end 83a of the third wiring 83, the end 82a of the second wiring 82, and the end 81a of the first wiring 81 are disposed in a line or parallel at equal intervals on the right edge 71 of the sensor sheet 2. Also, on the left edge 72, the end 83b of the third wiring 83 and the end 82b of the second wiring 82 are disposed at positions that are opposite or correspond to the end 82a of the second wiring 82 and the end 81a of the first wiring 81 on the right edge 71 respectively.

Accordingly, by aligning the sensor sheets 2a, 2b, and 2c as shown in FIG. 7, the end 81a of the first wiring 81 on the right edge 71 of the third sensor sheet 2c is connected to the end 82b of the second wiring 82 on the left edge 72 of the second sheet 2b. The end 82a of the second wiring 82 and the end 81a of the first wiring 81 of the right edge of the second sheet 2b are respectively connected to the end 83b of the third wiring 83 and the end 82b of the second wiring 82 on the left edge 72 of the first sheet 2a.

As shown in FIG. 7, the output of the data input region 75 of the third sensor sheet 2c is supplied to the control box 1 via the first wiring 81 of the third sensor sheet 2c, the extension wiring (the second wiring) 82 of the second sensor sheet 2b, and the extension wiring (the third wiring) 83 of the first sensor sheet 2a.

In the same way, the output of the data input region 75 of the second sensor sheet 2b is supplied to the control box 1 via the first wiring 81 of the second sensor sheet 2b, and the extension wiring (the second wiring) 82 of the first sensor sheet 2a.

The output of the data input region 75 of the first sensor sheet 2a is supplied to the control box 1 via the first wiring 81 of the first sensor sheet 2a.

In the biological information detection system 30, by merely connecting the three sensor sheets 2a, 2b, and 2c, the outputs of the individual sensor sheets 2a, 2b, and 2c can be inputted into a common control box 1 to which the first sensor sheet 2a is attached. It is possible, from the sheet assembly 60, to obtain data from the individual pressure sensors 7 in the control box 1 as if the sheet assembly 60 were a single sensor sheet.

It should be noted that the third wiring 83 of the second sensor sheet 2b and the third wiring 83 and the second wiring 82 of the third sensor sheet 2c are all unused wiring that is not connected. However, by providing extension wiring 82 and 83 of the same format that extends from the left edge 72 to the right edge 71 on each of the sensor sheets 2a, 2b, and 2c as described above, a plurality of sensor sheets can be connected easily, even if some of the wiring is not used.

The biological information detection system 30 that is of a suitable size for a semi-double bed is not formed of a single sensor sheet of a size that is suited to a semi-double bed, but is formed by linking together sensor sheets of a single-bed size or of a much smaller size. This means that a biological information detection system 30 of a suitable size for other size of bed can also be formed by linking together sensor sheet of the smaller size at low cost. If the number of linked sensor sheets is set at two, the size of the sheet assembly 60 is reduced to approximately ⅔ of the above size that is suitable for a single bed. It is also possible to construct a biological information detection system 30 with one sensor sheet 2 that is suited to a much smaller bed and/or to the stature of the user and the desired application.

Regarding the yield when manufacturing the sensor sheets, small-sized sensor sheets contain fewer sensors and elements compared to large-sized sensor sheets, which increases the yield rate. This also means that manufacturing costs can be reduced. Accordingly, by using the assemble type small-sized sensor sheets, it is possible to provide input/output systems of a variety of sizes at low cost, so that it is possible to provide biological information detection systems that can be easily used in hospitals, in the home, etc. When not in use, the system can be disassembled into the small-sized sensor sheets and stored, and even if one of the sensor sheets becomes faulty, replacement can be performed in units of the small-sized sensor sheets.

On the sensor sheets 2a, 2b, and 2c, the extension wiring 82 and 83 is disposed on the opposite side of the first wiring 81 to the data input region 75, so that the wiring can be laid out on a plane without the wires crossing. This means that all of the wiring can be formed by printing an electrode pattern on the sensor sheet. Few surface irregularities (convexes and concaves) are produced by the wiring and the region occupied by the wiring can be thin. This means that the entire sensor sheet 2 can be made thin, which makes it possible to provide a biological information detection system 30 which can be laid on bedding without causing much discomfort for the patient (user) 61, thereby allowing the patient to rest comfortably. The wiring pattern that forms the extension wiring or wire sets 82 to 83 can be produced simultaneously with the formation of the pressure sensors 7 and the wiring pattern for connecting the pressure sensors 7 and the first wiring 81, so that there is no increase in the number of manufacturing steps and the sensor sheets can be manufactured at low cost.

Figure 10:
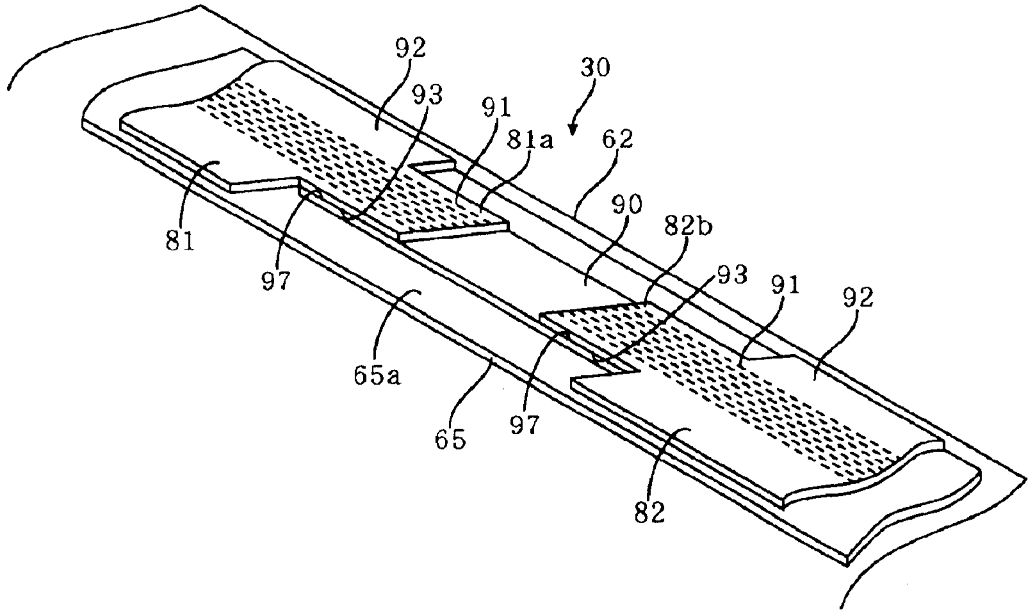
FIG. 10 is a perspective view showing an enlargement of an example connection between the second wiring of a first sensor sheet and the first wiring of a second sensor sheet.
Figure 11:
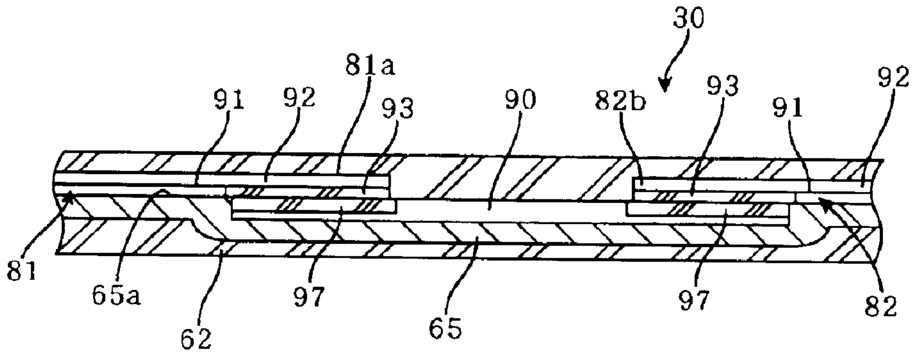
FIG. 11 is a perspective view showing the connected state shown in FIG. 10.

The right end 81*a* of the first wiring 81 is opposite the left end 82*b* of the second wiring 82 and the right end 82*a* of the second wiring 82 is opposite the left end 83*b* of the third wiring 83. Accordingly as shown in FIGS. 10 and 11, these wires can be connected by flexible cables 90 that extend perfectly straight between the sets of wiring. As one example, conductor wires 91 for connecting a plurality of piezoelectric sensors 7 and a covering 92 that covers the conductor wires 91 are provided on each of the second wiring 82 and the first wiring 81, so that by removing a lower part of the covering 92 at each of the ends 81*a* and 82*b* of the respective sets of wiring, electrodes 93 for connection are formed in advance at each edge 71 and 72. Accordingly, by connecting the electrodes 93 by welding or by conductive adhesive to electrodes 97 of the flexible cables 90, the sheets can be easily connected together.

The extension wiring 82 and 83 may be disposed in straight lines and connected using bending or angled connecting wiring materials. However, the durability of flexible cables deteriorates when the cables are bent, and large surface irregularities (convexes and concaves) are produced at the parts where the sensor sheets are connected, which may cause discomfort for the subject. If there is so wider space for connecting between the terminals 81*a* and 82*b*, risk of discomfort may be decreased, though if such wider space are located between the terminals, there is the possibility of the wires becoming twisted and overlapping one another, so that the problem described above may not be solved.

On the sensor sheet 2 shown in this specification, the wiring 82 and 83 is arranged on a single plane using angled arrangement in the sheet so as to the terminals are connected in a straight line and the distance between the terminals are minimized. Accordingly, the all of problem described above are solved.

Parts 98 that are internally curved cuts are provided on each of the sensor sheets 2*a*, 2*b*, and 2*c* at positions corresponding of the first edge 71 and the second edge 72. By the parts 98, as shown in FIG. 7, it is possible to easily bend over the sensor sheets 2 via these parts 98 along the dot-dash line X, so that the system can be compactly arranged during storage or transportation without damaging individual sensor sheets 2*a*, 2*b*, and 2*c* or the sheet assembly 60. In the sheet assembly 60, small intervals 94 are provided between the individual sensor sheets 2*a*, 2*b*, and 2*c* when the sensor sheets 2*a*, 2*b*, and 2*c* are stuck onto the base sheet 65, so that the sheet assembly 60 can be folded over at the boundaries (shown by the dot-dash lines Y in FIG. 8) between the individual sensor sheets without damaging the sensor sheets.

While the above describes a case where three sensor sheets are linked together, it is also possible to provide a biological information detection system 30 equipped with a sheet assembly 60 of an appropriate size that is composed of two sensor sheets or one sensor sheet. It is also possible to form an appropriate sheet assembly by connecting four or more sensor sheets, though in such case it is necessary to provide extension wiring in advance for the maximum number of sensor sheets to be connected. The positional relationship of the wiring region 76 and the data input/output region 75 is also not limited to the above example, and the wiring region may be disposed on the lower, left, or right edge of the data input/output region 75. If the wiring region is disposed on the left edge or the right edge and the wiring for extension such as the second and the third wirings extend in the longitudinal-direction of the bed, it becomes possible to link the sensor sheets in this longitudinal-direction.

The present invention is described by way of an example where pressure sensors are disposed in the data input/output region 75 of the sensor sheets, but temperature sensors or humidity sensors may be disposed in the data input/output region and other biological, biomedical or living information can be monitored. In addition, the sensor sheets described above represent one example of an input system equipped with a sheet-like input unit with a data input region. On the other hand by forming a data output region in which a plurality of flexible image elements, such as EL (electroluminescent elements), are aligned in the data input/output region of a sheet-like input/output unit, it is possible to apply the present invention to an output apparatus that has a sheet-like output unit, so that an output apparatus that is equipped with an expandable and flexible screen can also be provided according to the present invention.

What is claimed is:

1. A biological information detection system, comprising:

a sheet-like sensor unit that includes a sheet-like base material, a plurality of sensor elements disDosed thereon and wiring for the plurality of sensor elements; and a connection box that is attached to an edge of the sheet-like sensor unit and connected to the plurality of sensor elements via the wiring, wherein the connection box includes a housing that is attached so as to sandwich the edge of the sheet-like sensor unit and internally encloses a circuit board that is connected to the wiring, and the housing includes:

a slit through which the edge of the sheet-like sensor unit passes and whose upper and lower edges are curved shapes; and means for fixing the edae of the sheet-like sensor unit that is disposed behind the edges of the slit and inside of the housing.

2. A biological information detection system according to claim 1, wherein an edge, out of the upper and lower edges of the slit, that is above the sheet-like sensor unit is composed of a sealing part that is elastic.

3. A biological information detection system according to claim 1, wherein at least one hole formed in an area of the edge of the sheet-like sensor unit that is sandwiched by the housing, and wherein the means for fixing the edge of the sheet-like sensor unit includes at least one projection disDosed behind the edges of the slit for fixing the edae of the sheet-like sensor unit by being inserted into the at least one hole of the sheet-like sensor unit that is sandwiched by the edges of the slit.

4. A biological information detection system according to claim 1, wherein, in addition to the means for fixing the edge of the sheet-like sensor unit, the circuit board in the housing includes means for fixing a covering material of the wiring.

5. A biological information detection system according to claim 1, wherein a plurality of circuit boards are enclosed on top of one another inside the housing and the circuit board to which the wiring is connected is disposed at the bottom of the plurality of circuit boards.

6. A bioloaical information detection system according to claim 1, wherein the sheet-like sensor unit includes a data input region in which the plurality of sensor elements are disposed and a wiring region that is disposed along a side of the data input region.

7. A biological information detection system according to claim 1, wherein the sensor elements are piezoelectric sensor elements, and the sheet-like sensor unit includes a data input region where the plurality of sensor elements are disposed wiring region that is disposed along a side of the data input region, the wiring region includes first wiring that extends from the data input region to a first edge of the sheet-like sensor unit, and second wiring that is not connected to the data input region and extends from the first edge of the sheet-like sensor unit to a second edge opposite to the first edge, the connection box is disposed on the first edge, and the first wiring and the second wiring are connected to the circuit board.

8. A bioloalcal information detection system according to claim 7, wherein the second wiring is disposed on an opposite side of the first wiring to the data input region, and on the first edge, the first wiring and the second wiring are disposed in parallel, and on the second edge, the second wiring is disposed at a position corresponding to a position of the first wiring on the first edge.

9. A biological information detection system according to claim 8, wherein the first wiring on the first edge of another sheet-like sensor unit is connected to the second wiring on the second edge of the sheet-like sensor unit.

10. A biological information detection system according to claim 8, wherein third wiring that is not connected to the data input region, that extends from the first edge to the second edge of the sheet-like sensor unit, and that is connected to the circuit board is also disposed in the wiring region, the third wiring is disposed on an opposite side of the second wiring to the data input region, the first wiring, the second wiring and the third wiring are disposed in parallel on the first edge, and on the second edge, the third wiring is disposed at a position corresponding to a position of the second wiring on the first edge.

* * * * *

UNITED STATES PATENT AND TRADEMARK OFFICE

CERTIFICATE OF CORRECTION

PATENT NO. : 6,942,624 B2
APPLICATION NO. : 10/602815
DATED : September 13, 2005

INVENTOR(S) : Shun Takizawa and Yuichi Minamiyama

It is certified that error appears in the above-identified patent and that said Letters Patent is hereby corrected as shown below:

Column 14, line 19, cancel the text in claim 1 beginning with “a plurality of sensor elements disDosed” to and ending with “sensor elements” in column 14, line 20, and insert the following: “a plurality of sensor elements disposed thereon and wiring for the plurality of sensor elements;”

Column 14, line 34, cancel the text in claim 1 beginning with “means for fixing the edae of the sheet-like sensor unit that” in column 14, line 34, and insert the following “means for fixing the edge of the sheet-like sensor unit that”;

Column 14, line 47, cancel the text in claim 3 beginning with “at least one projection” to and ending with “sensor unit” in column 14, line 49, and insert the following “at least one projection disposed behind the edges of the slit for fixing the edge of the sheet-like sensor unit”.

Column 15, line 7, cancel the text in claim 7 beginning with “the plurality of sensor elements” to and ending with “data input region” in column 15, line 9, and insert the following “the plurality of sensor elements are disposed and a wiring region that is disposed along side of the data input region.”

Signed and Sealed this

Twenty-fifth Day of July, 2006

JON W. DUDAS
*Director of the United States Patent and Trademark Office*